United States Patent [19]

Genese et al.

[11] 4,324,238

[45] Apr. 13, 1982

[54] EQUIPMENT SETS HAVING A COMBINED AIR BARRIER AND LIQUID SEQUENCING DEVICE FOR THE SEQUENTIAL ADMINISTRATION OF MEDICAL LIQUIDS AT DUAL FLOW RATES

[75] Inventors: Joseph N. Genese, Waukegan; Andrew J. Muetterties, Mundelein, both of Ill.

[73] Assignee: Abbott Laboratories, North Chicago, Ill.

[21] Appl. No.: 157,922

[22] Filed: Jun. 9, 1980

Related U.S. Application Data

[63] Continuation-in-part of Ser. No. 16,461, Feb. 28, 1979, Pat. No. 4,256,104.

[30] Foreign Application Priority Data

Feb. 5, 1980 [AU] Australia ............................ 55234/80

[51] Int. Cl.³ .............................................. A61M 5/00
[52] U.S. Cl. .................................. 128/214 G; 55/159; 137/113; 222/145; 128/274
[58] Field of Search ............ 128/214 R, 214 C, 214 G, 128/214.2, 227, 274; 222/129.2, 145; 137/112–114, 183, 197–199; 55/159

[56] References Cited

U.S. PATENT DOCUMENTS

| | | | |
|---|---|---|---|
| 2,999,499 | 6/1961 | Willet | 128/214 G |
| 3,216,418 | 11/1965 | Scislowicz | 128/214 G |
| 3,217,711 | 11/1965 | Pelina et al. | 128/113 X |
| 3,886,937 | 6/1975 | Bobo et al. | 128/214 C |
| 3,993,066 | 11/1976 | Virag | 128/214 C |
| 4,116,646 | 9/1978 | Edwards | 55/159 |
| 4,136,693 | 1/1979 | Dyke | 128/214 C |
| 4,223,695 | 9/1980 | Muetterties | 128/214 G |
| 4,250,879 | 2/1981 | Muetterties | 128/214 G |

*Primary Examiner*—Stephen C. Pellegrino
*Attorney, Agent, or Firm*—Robert L. Niblack; Robert S. Beiser

[57] ABSTRACT

Equipment sets for the sequential administration of medical liquids allow primary liquid to be administered at a flow rate independent of the flow rate of a secondary liquid. The sets include a combined air barrier and liquid sequencing device to prevent the inadvertent administration of air when secondary liquid is depleted. The device also prevents the flow of primary liquid when secondary liquid is being dispensed.

12 Claims, 5 Drawing Figures

EQUIPMENT SETS HAVING A COMBINED AIR BARRIER AND LIQUID SEQUENCING DEVICE FOR THE SEQUENTIAL ADMINISTRATION OF MEDICAL LIQUIDS AT DUAL FLOW RATES

BACKGROUND OF THE INVENTION

This application is a continuation-in-part of U.S. patent application Ser. No. 16,461 filed Feb. 28, 1979, now U.S. Pat. No. 4,256,104.

The present invention relates to systems and equipment sets for the administration of medical liquids to a patient, and more particularly, to systems and equipment sets for the sequential administration of a plurality of medical liquids.

The parenteral administration of medical liquids to patients is a long established practice. Liquids including amino acids, blood, dextrose, electrolytes, and saline are commonly administered to patients over prolonged periods of time. Generally, these liquids are administered from a glass bottle or plastic bag suspended above the patient and containing 250–2,000 ml. of the liquid. Such prolonged infusions commonly are administered at a flow rate of 10–150 ml./hr.

Frequently, the patient must receive an additional or secondary liquid while the prolonged infusion is being administered. Preferably, this secondary liquid should be administered through the same hypodermic needle to avoid unnecessary pain and trauma to the patient of additional venipunctures. To avoid dilution and incompatability problems, it is also preferable that the primary flow be temporarily interrupted, the secondary liquid administered and the flow of the primary liquid resumed. Generally, the secondary liquid will be administered at a flow rate of 50–250 ml./hr.

Abbott Laboratories, North Chicago, Illinois manufactures a y-type set for the sequential administration of primary and secondary liquids. These VENOSET® piggyback sets allow the prolonged infusion of a primary liquid to be temporarily halted by means of a backcheck valve in the primary liquid flow path in order to administer a secondary liquid without the need for a new venipuncture. Then, when the secondary liquid has been depleted, the backcheck valve automatically opens to resume flow of the primary liquid. An important characteristic of this system is that the secondary liquid container must be suspended at a higher height than the primary liquid container to establish the liquid pressure differential that closes the backcheck valve in the primary liquid flow path.

A similar system is disclosed in U.S. Pat. No. 3,886,937 granted June 3, 1975 to D. Bobo, et al., assigned to American Hospital Supply Corp., and entitled "Medical Administration Set for Dispensing Plural Medical Liquids". Another similar system is disclosed in U.S. Pat. No. 4,105,029 granted Aug. 8, 1978 to R. Virag, assigned to Baxter Travenol Laboratories Inc. and entitled "Intravenous Solution Sets Having An Air Access Site and Constricted Inner Diameter Portion". Float type valves for such systems are illustrated by U.S. Pat. No. 4,175,558 granted Nov. 27, 1979 and assigned to Baxter Travenol Laboratories, Inc.

An inherent disadvantage of all of the abovementioned prior art medical liquid administration systems is that they each resume the flow of primary liquid at the rate the secondary liquid had been flowing. Because the preferred flow rate of the secondary liquid is generally greater than the preferred flow rate of the primary liquid, when the primary liquid resumes flow at that rate, the patient can be administered an excessive amount of primary liquid, unless the flow rate of the primary liquid is adjusted to the preferred primary flow rate soon after the flow of primary liquid resumes.

A remedy to the above-described disadvantage would appear to be provided by simply incorporating flow control devices into both the primary and secondary liquid flow paths. However, while this remedy does provide dual flow rates for the primary and second liquids, it is unacceptable. That is, because the common tube of the y-set must be able to accommodate both flow rates, when the primary liquid is flowing at a slower rate than the secondary liquid was, there will be an unfilled volume or void in the common tube. To fill that void, air will be drawn into the common tube from the depleted secondary container. That air will then be driven into the patient by the weight of the primary liquid, thereby causing a serious embolism and perhaps, the patient's death.

Accordingly, it will be apparent that an efficacious system for the sequential administration of medical liquids at dual flow rates would be advantageous to the medical profession.

SUMMARY OF THE INVENTION

The primary advantage of the present invention is to provide an equipment set for the sequential administration of medical liquids at dual flow rates, that will not draw air from the secondary container when the secondary liquid has been depleted. In accordance with this and other advantages, there is provided by the present invention an equipment set for the sequential administration of medical liquids to a patient comprising a primary tube for the flow of primary liquid, a secondary tube for the flow of secondary liquid, a common tube in fluid communication with the primary and secondary tubes, a primary flow control and a secondary flow control. Further included is a combined air barrier and liquid sequencing device which comprises a housing having a first chamber connected to the primary tube and the second chamber connected to the secondary tube. Both chambers have inlet and outlet ports. An outlet port located between the second chamber and the first chamber, permits the passage of secondary liquid from the second chamber into the first chamber, but prevents the passage of air from the second chamber into the first chamber. A check valve is also incorporated into the device which prevents primary liquid from flowing through the system when the pressure of the secondary liquid exceeds the pressure of the primary liquid, such as when a container of secondary liquid is positioned higher than the primary liquid. A vent mechanism permits air to pass from the combined air barrier and liquid sequencing device, when priming the system, so that when liquid is admitted into the system, air within the tubing and the device rises and is dispersed through the venting mechanism.

In a preferred embodiment of the invention the first chamber of the device has an inlet port at the top and an outlet port at the bottom. The first chamber is positioned below the second chamber. As a result, the previously mentioned check valve mechanism normally seals the outlet port from the second chamber to the first chamber during dispensing of primary liquid. The check valve mechanism opens to allow passage of secondary liquid into the first chamber during dispensing of secondary liquid. In this embodiment, a float valve is positioned across the outlet port from the second chamber into the first chamber. The float normally covers the outlet port from the second chamber but rises within the second chamber in the presence of secondary liquid due to the positive buoyancy of the float. As a result, secondary liquid is allowed to pass through the outlet port into the first chamber. When the secondary liquid is not being dispensed, the float returns to the covered position over the port. Alternatively, the valve mechanism may comprise a hydrophilic membrane positioned across the port from the second chamber into the first chamber. When primary liquid is running through the system for priming the device, air may pass from the first chamber through the second chamber and out at the top of the device. When secondary liquid is running through the system, the hydrophilic membrane allows the passage of the secondary liquid but then prevents the passage of air upon depletion of secondary liquid.

The previously described equipment set is preferably used in a gravitational flow system for sequential administration of medical liquids to a patient. Included in the system are a primary container suspended in space for containing a primary liquid and a secondary container suspended in space at a height greater than that of the primary container for containing a secondary medical liquid. The previously mentioned primary and secondary tubes are connected respectively to the primary and secondary containers. In a preferred embodiment, the secondary flow control is on the common tube. However, alternatively, the secondary flow control may be on the secondary tube extending from the combined air barrier and liquid sequencing device. The flow of secondary fluid is preferentially faster than that of the primary liquid so that such a flow control would have no effect on the flow of primary liquid.

An additional feature of the invention is the use of a chamber having a compressible mass in fluid communication with the primary tube which provides a spring for relieving pressure on the distal side of the primary valve whenever the height of the primary liquid is less than the height of the secondary liquid in the system. This chamber has inlet and outlet ports in communication with the primary tube. In a preferred embodiment, the compressible mass is air.

The distal ends of the primary and secondary tubes may include piercing pins which are inserted into the primary and secondary containers. The containers may be either rigid or flexible. The piercing pins may have filtered air vents thereon, and may include an integral drip chamber.

DETAILED DESCRIPTION OF THE PREFERRED EMBODIMENT

Figure 1:
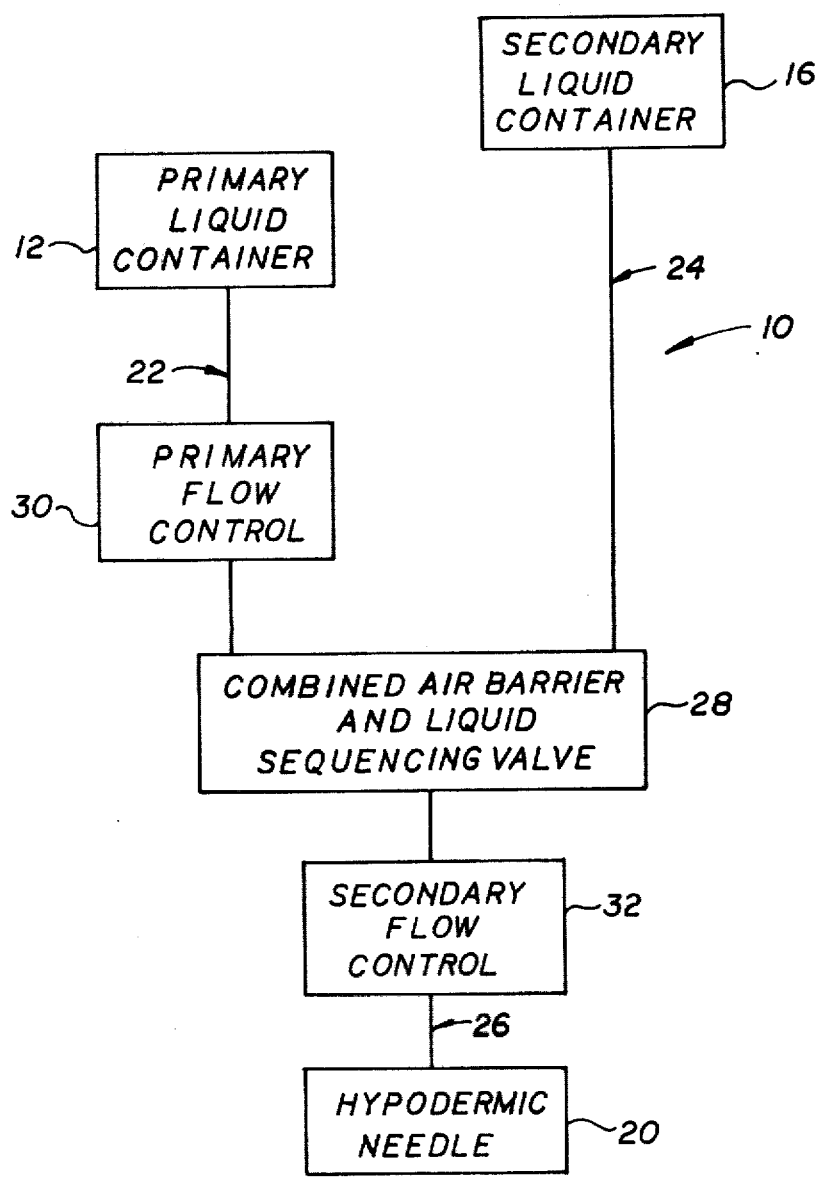
FIG. 1 of the drawings is a schematic diagram of an improved gravitational flow system for the sequential administration of medical liquids.

While this invention is susceptible of embodiment in many different forms, there is shown in the drawings and will herein be described in detail, several specific embodiments, with the understanding that the present disclosure is to be considered as an exemplification of the principles of the invention and is not intended to limit the invention to the embodiments illustrated.

Figure 2:
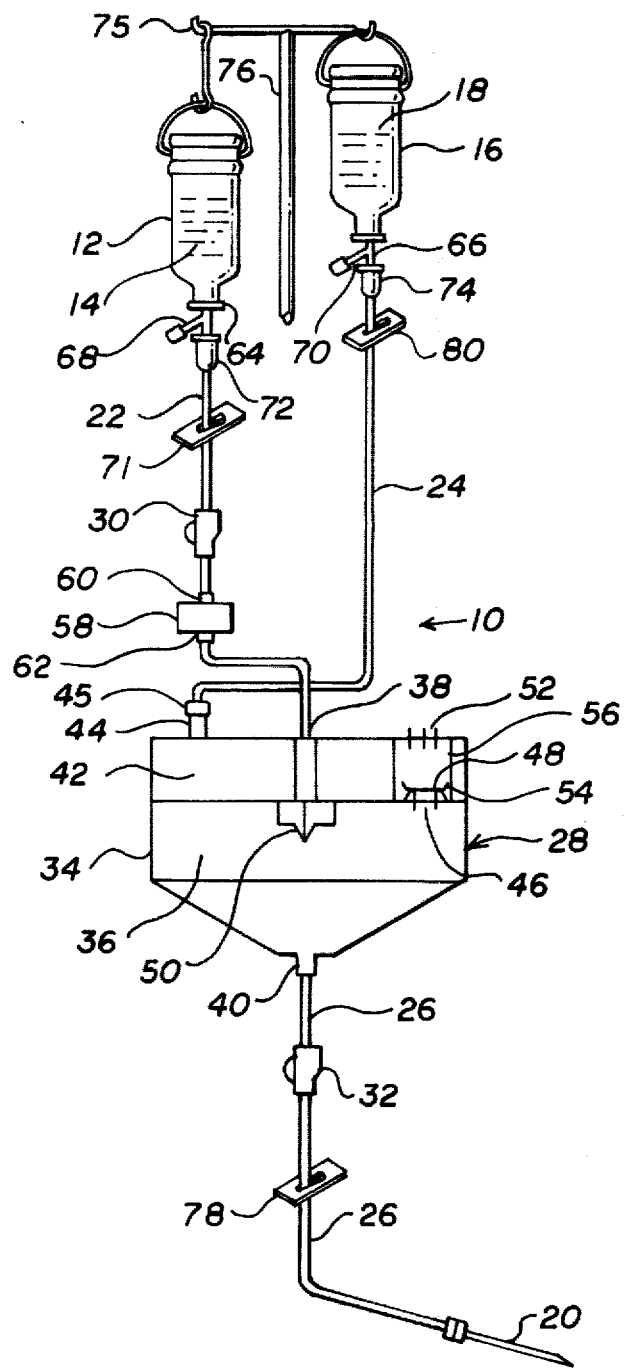
FIG. 2 of the drawings is a side view partially broken away of the improved gravitational flow system of FIG. 1.

Referring to the drawings, there is shown in FIG. 1 a schematic block diagram of the basic elements of a gravitational flow system 10 for the sequential administration of medical liquids at dual flow rates contemplated by this invention. The diagram depicts a primary liquid container 12 that contains a primary medical liquid 14, such as a solution, to be administered to a patient for a prolonged period of time. The diagram also depicts a secondary liquid container 16 that contains a secondary medical liquid 18, such as an antibiotic, to be administered to the patient for a relatively short period of time, during which the administration of the primary liquid will be temporarily interrupted. As shown in FIG. 2, containers 12 and 16 are glass bottles. However, plastic flexible bags, or any other suitable container could be used.

Primary container 12 and secondary container 16 are connected to and in fluid communication with a hypodermic needle 20 through a primary tube 22, a secondary tube 24 and a common tube 26. Thus, the primary liquid flow path from primary container 12 to needle 20 comprises primary tube 22 and common tube 26. Likewise, the secondary liquid flow path from secondary container 16 to needle 20 comprises secondary tube 24 and common tube 26.

Interposed between primary tube 22, secondary tube 24 and common tube 26 is the combined air barrier and liquid sequencing device 28. Device 28 allows primary liquid 14 to flow from primary container 12 whenever the height of primary container 12 is greater than or equal to the height of secondary liquid 18 in system 10, and prevents primary liquid 14 from flowing when the height of primary container 12 is less than the height of secondary liquid 18 in system 10.

Additionally, shown in FIGS. 1 and 2, is primary flow control 30 interposed between primary container 12 and combined air barrier and liquid sequencing device 28. Secondary flow conrol 32 is positioned on common tube 26 between combined air barrier and liquid sequencing device 28 and hypodermic needle 20. Since secondary flow is generally faster than primary flow, as best seen in FIG. 2 of the drawings, primary flow control 30 and secondary flow control 32 comprise conventional roller clamps. However, other commonly known means of flow control such as screw clamps or needle valves may be employed.

As seen in FIG. 2, combined air barrier and liquid sequencing device 28 comprises housing 34 having a first chamber 36. First chamber 36 includes inlet port 38 and outlet port 40. Housing 34 also includes second chamber 42 which includes inlet port 44 and outlet port 46. Inlet port 44 is preferably covered by a resilient penetrable rubber reseal 45. Proximate outlet port 46 is a valve mechanism 48 which is constructed for permitting the passage of secondary liquid from second chamber 42 into first chamber 36. At the same time, valve mechanism 48 prevents the passage of air from second chamber 42 into first chamber 36 when secondary liquid 18 is not being dispensed.

An additional feature of liquid sequencing device 28 is a check valve mechanism 50 which prevents primary liquid from flowing through the primary flow path when secondary liquid is being dispensed. This is due to the fact that the pressure of the secondary liquid 18 is greater than that of the primary liquid 14 due to primary container 16 being disposed at a lower elevation than secondary container 16. As a result, check valve 50 remains in a closed position preventing the passage of primary liquid from primary tube 22.

Figure 3:
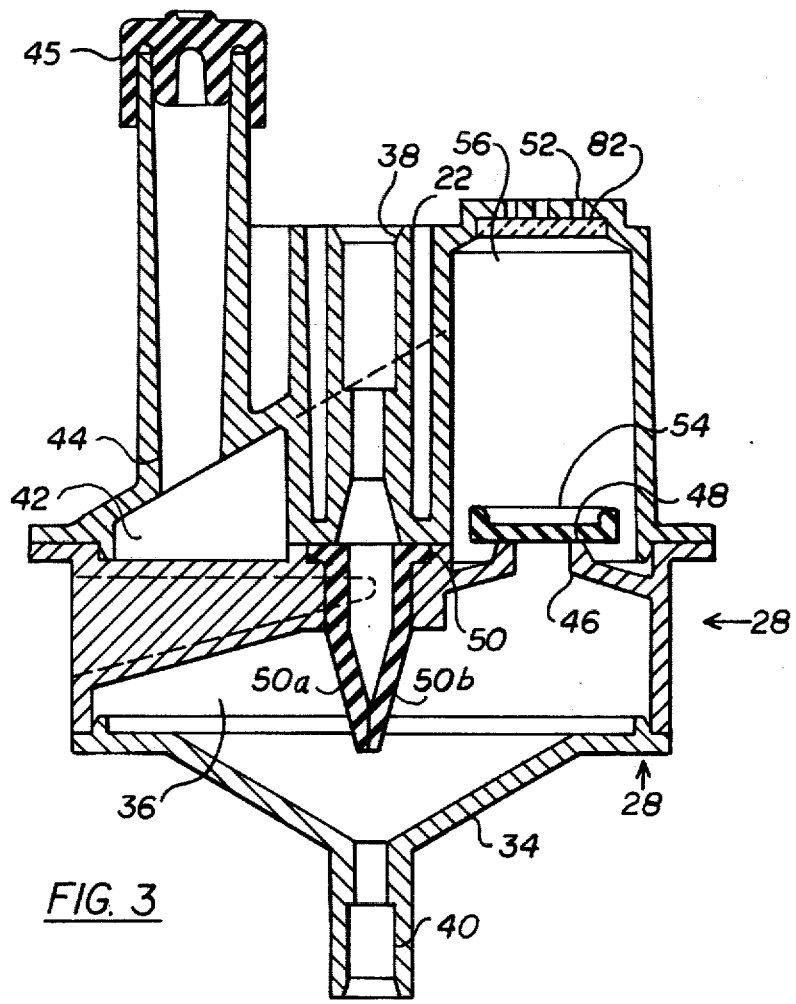
FIG. 3 of the drawings is a vertical section of an improved, combined air barrier and liquid sequencing device, as seen in FIG. 2.

As best seen in FIG. 3, in a preferred embodiment, check valve 50 comprises a resilient rubber duck bill valve whose lips 50a and 50b are opened by the pressure of primary liquid 14, and closed by the pressure of secondary liquid 18. However, other types of commonly known valve mechanisms may be used.

An additional feature of the invention is vent mechanism 52 which allows the passage of air from combined air barrier and liquid sequencing device 28, when priming the system 10. Where vent mechanism 52 not present, air would be trapped within secondary chamber 42. In addition, vent mechanism 52 permits valve mechanism 48 to reseal port 46 between first chamber 36 and second chamber 42 upon depletion of secondary liquid 18.

In a preferred embodiment, as seen in FIG. 3, first chamber 36 has inlet port 38 at the top thereof and outlet port 40 at the bottom thereof. First chamber 36 is positioned below second chamber 42 so that valve mechanism 48 normally seals outlet port 46 during dispensing of primary liquid 14 but opens to allow passage of secondary liquid 18 during dispensing of secondary liquid 18. As shown, valve mechanism 48 comprises a float valve member 54 positioned over outlet port 46, which normally covers outlet port 46 during dispensing of primary liquid. However, when secondary liquid 18 enters second chamber 42, float valve member 54 rises within portion 56 of second chamber 42. Float valve member 54 is of positive buoyancy, i.e., its specific gravity is lower than 1 so as to rise within secondary liquid 18. As a result, port 46 is open and secondary liquid passes through port 46 into first chamber 36 and out of housing 34 by means of port 40. In addition, upon entrance into first chamber 36, secondary liquid 18 is under greater pressure than primary liquid 14. Consequently, secondary liquid 18 causes check valve mechanism 50 to seal port 38. Alternatively, valve mechanism 48 could comprise a hydropholic membrane which would allow the passage of primary or secondary liquid but prevent the passage of air.

An additional feature of the invention, as seen in FIG. 2 of the drawings, is the inclusion of chamber 58 in primary tube 22 between primary flow control 30 and combined air barrier and liquid sequencing device 28. Chamber 58 contains a compressible mass which acts as a spring for relieving pressure on the distal side of combined air barrier and liquid sequencing valve 28 as secondary liquid is initially dispensed. As shown chamber 58 has an inlet port 60 and an outlet port 62 in fluid communication with primary tube 22. In a preferred embodiment, the compressible mass within chamber 58 is air.

Primary tube 22 and secondary tube 24 at their distal ends may include piercing pins 64 and 66, for connection with and fluid communication to primary container 12 and secondary container 16. Additionally, piercing pins 64 and 66 may include filtered air vents 68 and 70 and drip chambers 72 and 74. Primary container 12 and secondary container 16 may be commonly known rigid or flexible containers used in the medical solution field.

Figure 4:
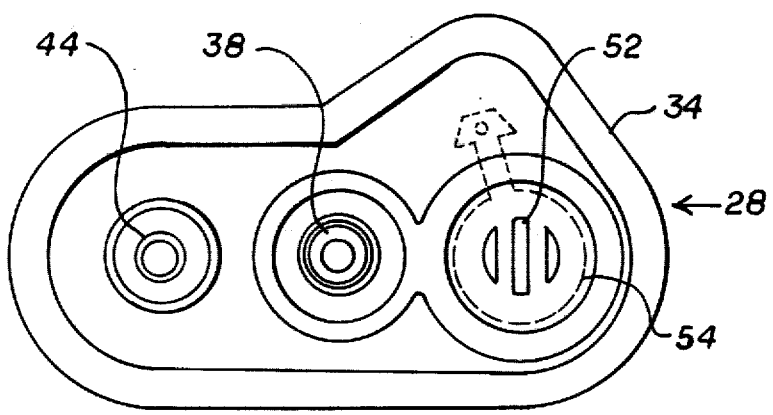
FIG. 4 of the drawings is a top view of the improved, combined air barrier and liquid sequencing valve of FIG. 3.

As best seen in FIG. 4 of the drawings, inlet ports 38 and 44 and venting mechanism 52 are disposed across the top of housing 34 in order to provide simple and easy access to connect an air barrier and liquid sequencing valve to system 10.

OPERATION OF THE SYSTEM

As depicted in FIG. 2, primary container 12 is suspended in space at a height above the patient by means of a hook 75, a stand 76 or other commonly known means for suspending containers. To insure that all air that might be forced into the patient has been removed from the set, set 10 is initially primed by first closing slide clamps 71, 78 and 80. Piercing pin 64 is then inserted into the releasable closure of primary container 12. Primary flow control 30 is fully opened. Slide clamps 71 and 78 are then opened to allow primary liquid to flow through the primary liquid flow path and force all the air therefrom that might be forced into the patient. Secondary flow control 32 is then opened to allow primary liquid to flow through tube 26. Primary liquid 14 will then flow from primary container 12 through primary tube 22, inlet port 38, check valve mechanism 50, first chamber 36, outlet port 40, common tube 26 and out hypodermic needle 20. Slide clamp 78 may then be closed to cut off flow of primary liquid 14. Air will be retained in second chamber 42 as the flow rate of primary liquid 14 is not sufficient to completely fill the second chamber.

Figure 5:
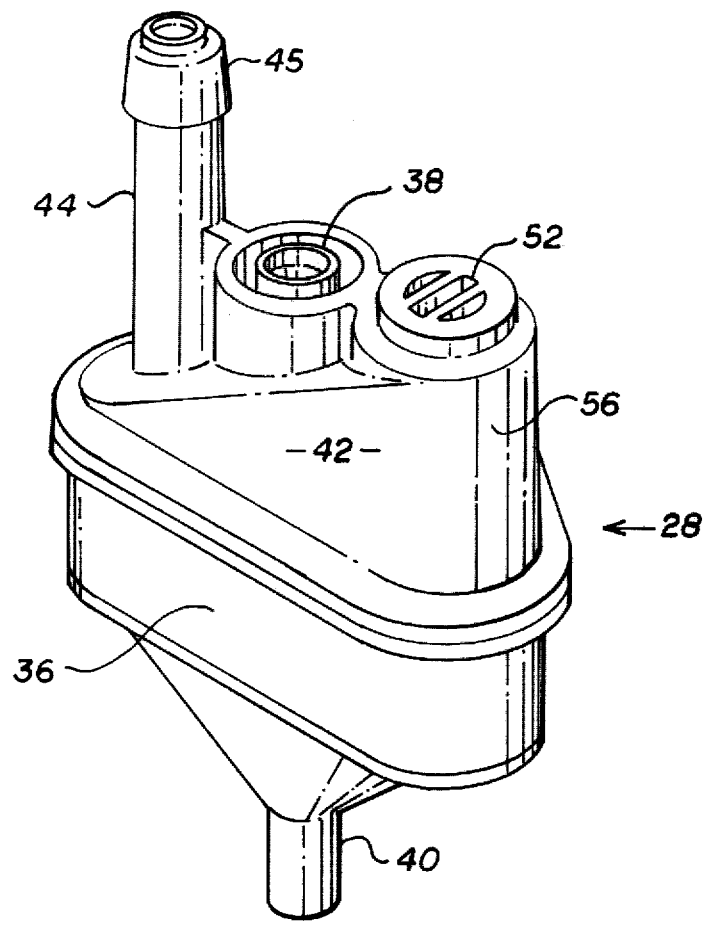
FIG. 5 of the drawings is a front perspective view of the improved combined air barrier and liquid sequencing device seen in FIGS. 2-4.

When use of secondary liquid is desired, slide clamp 80 is opened and piercing pin 66 is inserted into the releasable closure of container 16. Secondary liquid 18 will then flow through secondary tube 24 and port 44 into second chamber 42. As seen in FIGS. 3 and 5, housing 34 is circular so that secondary liquid 18 will pass around second chamber 42 and into portion 56, which will lift float valve member 54 allowing the passage of secondary liquid 18 into first chamber 36. Because secondary liquid 18 is under greater pressure than primary liquid 14, the presence of secondary liquid 18 in first chamber 36 will cause check valve 50 to cut off the flow of primary liquid 14. Any air within second chamber 42 will then pass the top of portion 56 and out of vent mechanism 52. It should be noted in this regard that vent mechanism 52 may comprise a hydrophobic membrane 82. Secondary liquid 18 will then pass from first chamber 36 by means of port 40, through common tube 26 and out of hypodermic needle 20. When the height of secondary liquid 18 descends to a level equal to or lower than the height of primary liquid 14, float valve member 54 will lower until it again reseals port 46. At this point, primary liquid 14 will again begin to flow.

The foregoing description and drawings merely illustrate and explain the invention, and the invention is not limited thereto except insofar as those skilled in the art who have the disclosure before them will be able to make modifications and variations therein without departing from the scope of the invention.

I claim:

1. A set for the sequential administration of medical liquids to a patient, comprising:
    a primary tube for the flow of a primary medical liquid therethrough, a secondary tube for the flow of a secondary medical liquid therethrough, a common tube having its distal end in fluid communication with the proximal ends of said primary and secondary tubes and its proximal end open for the flow of liquid therethrough to form a primary liquid flow path comprising said primary tube and said common tube and a secondary liquid flow path comprising said secondary tube and said common tube, a secondary flow control means in said secondary liquid flow path for adjusting the flow rate of said secondary liquid therethrough, a primary flow control means on said primary tube for adjusting the flow rate of said primary liquid through said primary flow path to a rate independent of the flow rate of said secondary liquid through said secondary liquid flow path, and combined air barrier and liquid sequencing means comprising a housing having a first chamber which constitutes a portion of said primary tube and has inlet and oulet ports thereto and a second chamber which constitutes a portion of said secondary tube and has inlet and outlet ports thereto, said housing including;

valve means proximate said outlet port from said second chamber into said first chamber, said valve means being constructed and arranged for permitting the passage of said secondary liquid from said second chamber into said first chamber and for preventing of the passage of air from said second chamber into said first chamber when said secondary liquid is not being dispensed;

check valve means operatively associated with said first chamber for the prevention of primary liquid flow through said primary tube whenever said secondary liquid is being dispensed, and vent means operatively associated with said second chamber for permitting the passage of air from said combined air barrier and liquid sequencing valve, thereby permitting priming of said system.

2. The set defined in claim 1, wherein said second chamber has said inlet port at the top thereof and and said outlet port at the bottom thereof opening into said first chamber, said first chamber being positioned below said second chamber whereby said valve means normally seals said outlet port from said second chamber to said first chamber during dispensing of said primary liquid but opens to allow passage of said secondary liquid into said first chamber during dispensing of said secondary liquid.

3. The set according to claim 1 in which said valve means comprises a float valve member positioned proximate said outlet port from said second chamber into said first chamber whereby said float valve member normally covers said outlet port to said second chamber during dispensing of said primary liquid, but rises within said second chamber in the presence of said secondary liquid due to positive buoyancy so as to allow the passage of said secondary liquid through said outlet port into said first chamber.

4. The set according to claim 1 in which said valve means comprises a hydrophilic membrane.

5. The system defined in claim 1, wherein said secondary flow control means in on said common tube.

6. The system defined in claim 1, wherein said secondary flow control means is on said secondary tube.

7. The system defined in claim 1 and further including a chamber for a compressible mass in fluid communication with said primary tube between said primary flow control means and said combined air barrier and liquid sequencing valve to provide a spring for relieving pressures on the distal side of said combined air barrier and liquid sequencing valve during the initial cutoff of said primary liquid in said system due to the removal of said secondary liquid.

8. The system defined in claim 7, wherein said chamber has an inlet and outlet in communication with said primary tube.

9. The system defined in claim 7, wherein said compressible mass is air.

10. The system defined in claim 1, wherein said distal ends of said primary and secondary tubes include piercing pins having filtred air vents and said primary and secondary containers are rigid containers.

11. The system defined in claim 1, wherein said distal ends of said primary and secondary tubes include piercing pins and said primary and secondary containers are flexible containers.

12. The system defined in claim 10 or 11 wherein said piercing pins include an integral drip chamber.

* * * * *